US011794154B2

(12) United States Patent
Zeuch et al.

(10) Patent No.: US 11,794,154 B2
(45) Date of Patent: Oct. 24, 2023

(54) MIXING APPARATUS AND METHOD FOR OPERATING A MIXING APPARATUS

(71) Applicant: SARTORIUS STEDIM BIOTECH GMBH, Goettingen (DE)

(72) Inventors: Stefan Zeuch, Goettingen (DE); Markus Haeusser, Goettingen (DE); Stefan Weisshaar, Adelebsen (DE); Jens Ludwig, Juehnde (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 811 days.

(21) Appl. No.: 16/785,789

(22) Filed: Feb. 10, 2020

(65) Prior Publication Data
US 2020/0171450 A1 Jun. 4, 2020

Related U.S. Application Data

(63) Continuation of application No. PCT/EP2018/068050, filed on Jul. 4, 2018.

(30) Foreign Application Priority Data

Aug. 10, 2017 (DE) ...................... 10 2017 007 557.3

(51) Int. Cl.
*B01F 27/09* (2022.01)
*B01F 27/808* (2022.01)
(Continued)

(52) U.S. Cl.
CPC ............ *B01F 27/808* (2022.01); *B01F 27/90* (2022.01); *B01F 35/513* (2022.01); *B01F 2035/3513* (2022.01)

(58) Field of Classification Search
CPC ................... B01F 2035/351; B01F 2035/3511
(Continued)

(56) References Cited

U.S. PATENT DOCUMENTS 2,746,779 A * 5/1956 Lobanoff ................. F16J 15/54
  277/516
4,878,677 A * 11/1989 Larkins .................. F16J 15/183
  366/331
(Continued)

FOREIGN PATENT DOCUMENTS

DE 4127073 A1 2/1993
DE 202006014665 U1 11/2006
(Continued)

OTHER PUBLICATIONS

International Preliminary Report on Patentability and Written Opinion, PCT/EP2018/068050, dated Feb. 11, 2020, 5 pages.
(Continued)

*Primary Examiner* — David L Sorkin
(74) *Attorney, Agent, or Firm* — Edell, Shapiro & Finnan, LLC

(57) ABSTRACT

A mixing apparatus (1) for mixing a fluid and/or solid. The mixing apparatus includes a mixing container (100) having an interior in which the fluid and/or solid can be arranged. A feed-through passage (10) extends through a container wall (101) of the mixing container. A drive shaft (50) is fed through the feed-through passage, to drive a stirring element (30) arranged at least partly in the interior of the mixing container. The stirring element is used to mix the fluid and/or solid arranged in the mixing container. A drive-side shaft end (51) of the drive shaft couples the drive shaft to a drive (120) arranged outside of the mixing container. An adjustable seal (70) seals off the feed-through passage. A setting apparatus (80) is provided to switch the adjustable seal into at least two sealing operation states having different sealing effects.

19 Claims, 5 Drawing Sheets

(51) Int. Cl.
*B01F 27/90* (2022.01)
*B01F 35/513* (2022.01)
*B01F 35/30* (2022.01)

(58) Field of Classification Search
USPC .................................................. 366/331, 608
See application file for complete search history.

(56) References Cited

U.S. PATENT DOCUMENTS

| | | | |
|---|---|---|---|
| 6,193,409 B1 * | 2/2001 | Brunson | B01F 35/10 366/331 |
| 6,746,147 B2 * | 6/2004 | Blakley | F16J 15/008 277/630 |
| 7,237,778 B1 * | 7/2007 | Althouse, III | F16J 15/008 277/630 |
| 7,757,603 B2 * | 7/2010 | Bokelmann | A01J 25/06 99/465 |
| 7,780,340 B2 * | 8/2010 | Bokelmann | A61L 2/18 366/331 |
| 2002/0105856 A1 * | 8/2002 | Terentiev | B01F 35/146 366/279 |
| 2011/0058447 A1 | 3/2011 | Reif et al. | |
| 2016/0327159 A1 * | 11/2016 | Miller | F16J 15/008 |

FOREIGN PATENT DOCUMENTS

| | | | |
|---|---|---|---|
| EP | 2285478 B1 | 5/2012 | |
| WO | 2016179236 A1 | 11/2016 | |

OTHER PUBLICATIONS

International Search Report, PCT/EP2018/068050, dated Oct. 2, 2019, 4 pages.

* cited by examiner

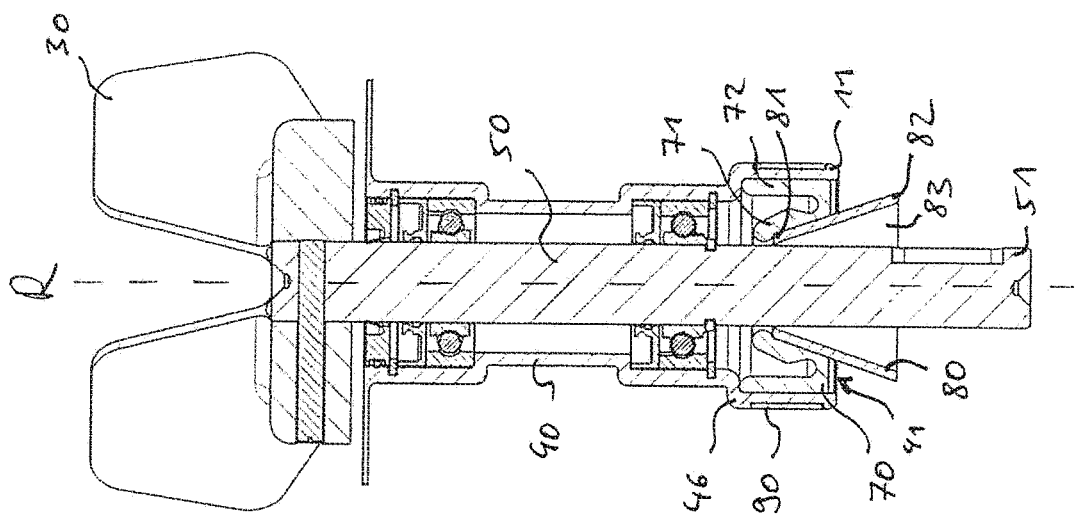
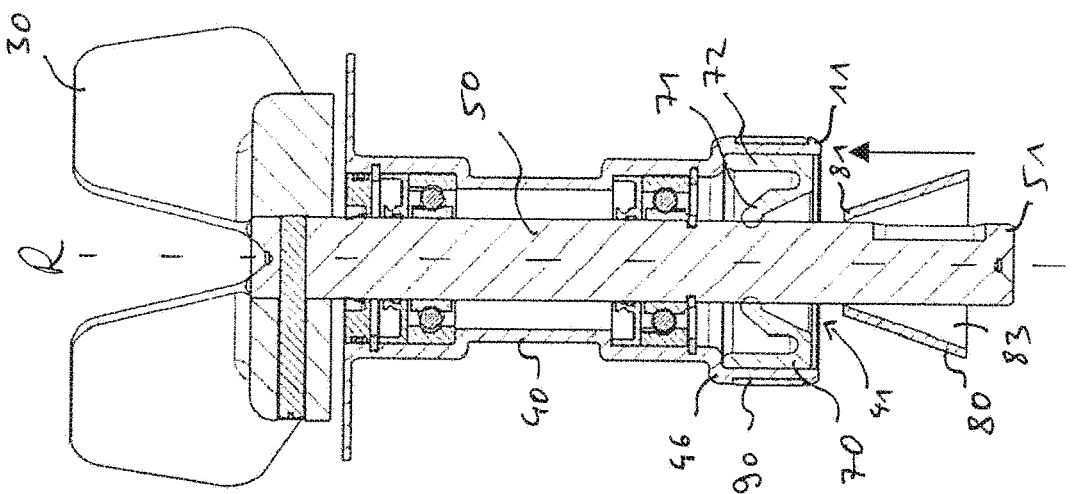
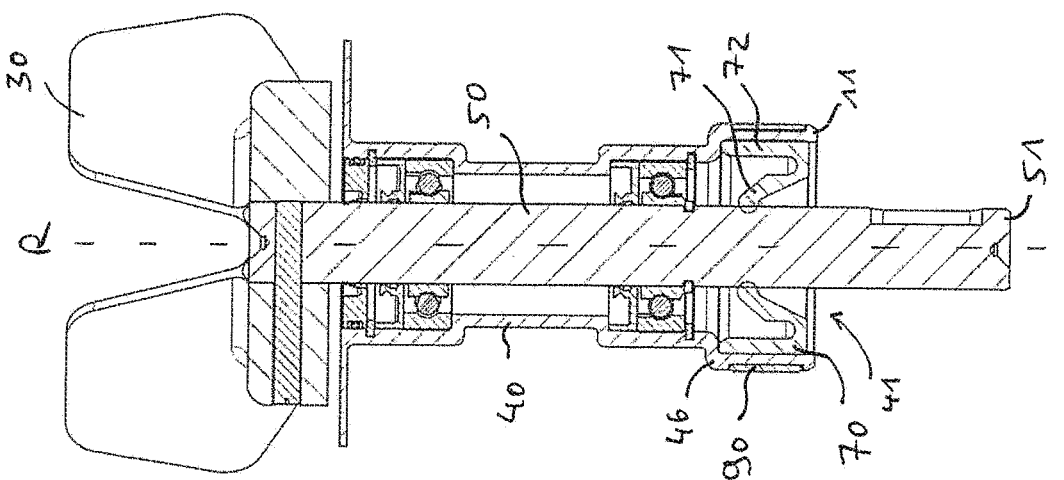

MIXING APPARATUS AND METHOD FOR OPERATING A MIXING APPARATUS

CROSS REFERENCE TO RELATED APPLICATIONS

This is a Continuation of International Application PCT/EP2018/068050 which has an international filing date of Jul. 4, 2018, and the disclosure of which is incorporated in its entirety into the present Continuation by reference. This Continuation also claims foreign priority under 35 U.S.C. § 119(a)-(d) to and also incorporates by reference, in its entirety, German Patent Application DE 10 2017 007 557.3 filed on Aug. 10, 2017.

FIELD OF INVENTION

The invention relates to a mixing apparatus and a method for operating a mixing apparatus.

BACKGROUND

Mixing apparatuses, which are provided, for example, for bioreactors, mixing bags and/or pallet tanks, are used to receive, to store, and/or to mix fluids and/or solids, such as, for example, biological media. In this case biological media may be provided in mixing containers, such as, for example, bags. Inside such a mixing container the biological media are introduced into the mixing apparatus, in which they can be stored, temperature-controlled and/or thoroughly mixed. Various analyses can be performed on the biological medium in such a mixing apparatus.

In this case the mixing apparatus is usually handled in a sterile environment. In so doing, the mixing of the fluid and/or solid can be carried out with a rotating stirring element, which is inserted into the mixing container and is driven from outside the mixing container. At the same time the media-contacting stirring element can be driven to rotate. In this case the drive for the stirring element, such as, for example, a motor, should not come into contact with the medium, so that it does not become contaminated and does not have to be cleaned and/or sterilized for a subsequent process. At a particularly critical point, however, a drive shaft may be inserted from the outside into the interior of the mixing container in order to be able to mix the medium located therein in a stirring manner. From an engineering point of view it is very difficult to insert a drive shaft, which rotates about its longitudinal axis, in a safe and sterile manner into the interior of the container in such a way that the interior of the container will remain leak-proof in relation to the exterior of the mixing container even under a rotational movement of the drive shaft.

SUMMARY

One object of the present invention is to provide an improved mixing system that allows, in particular, the driving force to be introduced into the fluid and/or the solid in a safe way.

This object is achieved by the subject matter recited in the independent claims. Preferred embodiments are the subject matters of the dependent claims.

One aspect relates to a mixing apparatus for mixing a fluid and/or solid, said mixing apparatus comprising a mixing container, in the interior of which the fluid and/or the solid can be arranged. The mixing container may be arranged in a mixing container receptacle of the mixing apparatus. The mixing apparatus has a feed-through extending through a container wall of the mixing container and a drive shaft, that extends through the feed-through, for driving a stirring element, which is arranged at least partly in the interior of the mixing container, in order to mix the fluid and/or solid, arranged in the mixing container. A drive-side shaft end of the drive shaft is designed for coupling a drive, arranged outside of the mixing container, to the drive shaft. The mixing apparatus has an adjustable seal for sealing the feed-through, wherein the adjustable seal can be put into at least two sealing operation states having different sealing effects.

The mixing apparatus may be designed, in particular, for mixing a mixing container, which may be designed as a bioreactor bag, pallet tank and/or as another mixing bag of the type described in the introductory part of this patent specification. In addition to the mixing container, which is designed to receive the fluid and/or the solid, the mixing apparatus may also comprise a mixing container receptacle for the mixing container. The mixing container receptacle may have a bearing arrangement, a coupling and/or a connector for supporting, coupling and/or connecting the mixing container. In particular, an inlet and/or an outlet for connecting to the mixing container may be formed on the mixing container receptacle. Furthermore, the feed-through may be formed at the mixing container in such a way that the drive shaft can be arranged through the feed-through into the interior of the mixing container. In order to receive the mixing container, the mixing apparatus may comprise the mixing container receptacle, in which the mixing container can be received in such a way that, for example, a drive-side end of the drive shaft may be coupled to a drive, arranged outside of the mixing container. The mixing apparatus may comprise the mixing container, instead of the mixing container receptacle. In particular, the mixing apparatus may also consist of just the mixing container, i.e., may be designed as the mixing container.

The fluid and/or the solid may be formed as a biological medium. Furthermore, the mixing container may also be designed to receive a fluid mixture and/or a solid mixture and/or may contain such a mixture.

The mixing container may be arranged at and/or in the mixing container receptacle of the mixing apparatus. The mixing container may be designed at least partially as a flexible bag, i.e., may comprise a flexible bag wall. As an alternative or in addition, the mixing container may comprise, at least partly, substantially stiff and/or rigid container walls, which may be, for example, metallic or formed of a hard plastic material. The mixing container may be designed as a so-called "single-use bag", i.e., as a disposable bag that can be disposed of after the mixing process. The mixing container contains the fluid and/or the solid that is/are mixed.

A movement of the stirring element, for example, a rotational movement, is used to mix the fluid and/or the solid. The rotational movement of the stirring element may take place about an axis of rotation, with the axis of rotation being arranged in such a way that the axis of rotation passes through the stirring element, for example, through a center point and/or the center of gravity of the stirring element.

The drive, which may be designed as a motor, in particular, an electric motor, which can be arranged outside of the mixing container and, thus, is not in contact with the media, is used to drive the stirring element. The drive may be designed as part of the mixing apparatus. As an alternative, the mixing apparatus itself may be designed without a drive and may be designed only to connect the drive to the drive shaft.

In this case the driving force of the drive is transmitted at least partly from the drive to the stirring element by way of the drive shaft. In other words, the drive drives the drive shaft, for example, to a rotational movement about an axis of symmetry of the drive shaft. The movement of the drive shaft can be transmitted to the stirring element.

The drive shaft may be arranged in such a way that it is arranged so as to point at least partly into the interior of the mixing container from outside of the mixing container. The end of the drive shaft that is arranged outside of and/or at the edge of the mixing container is designed as the drive-side shaft end, which may be and/or will be connected directly or indirectly to the drive. An opposite end of the drive shaft that points into the interior of the mixing container, in particular, an end, which is arranged in the interior of the mixing container, is connected directly or indirectly (for example, through a bearing arrangement and/or clutch) to the stirring element. This end is referred to as the stirring-side shaft end. The stirring-side shaft end is connected preferably rigidly and/or directly to the stirring element, so that the component cost is reduced, because, for example, no additional clutch is necessary.

The drive shaft may be designed so as to be substantially elongated, for example, in the shape of a cylinder, the cylinder axis of which is greater by a multiple than its diameter. The circumference of the cylinder may be designed so as to be, at least partly, round and/or at least partly angular or, more specifically, polygonal. The drive shaft may be arranged at least partly in such a way that the cylinder axis of the stirring rod coincides with the axis of rotation, about which the rotational movement of the stirring element takes place.

The drive shaft is fed through the container wall of the mixing container at the feed-through.

The feed-through may be formed as an opening and/or a recess. The feed-through may be designed so as to be reinforced, i.e., for example, may have a housing that at least partially surrounds and/or defines the feed-through. In other words, the container wall and optionally also the mixing container receptacle have a feed-through through the container wall, the inner diameter of which is at least as large as the outer diameter of the drive shaft. In this case the feed-through may be arranged, in particular, in a lower region of the mixing container. For example, the feed-through may be arranged centrally below the mixing container receptacle and/or the mixing container. In general, it may be necessary to provide seals, such as, for example, an O-ring at the feed-through, in order to reduce both contamination of the contents of the mixing container as well as leakage of the fluid or the solid out of the mixing container.

A plurality of seals may be formed and/or provided at the feed-through. One of the seals is designed as the adjustable seal. The adjustable seal can seal the feed-through in the at least two different sealing operation states. In this case the adjustable seal can be put from a first sealing operation state into a second sealing operation state and vice versa. In other words, the adjustable seal is repeatedly adjustable, for example, reversible between two different sealing operation states.

In this case the adjustable seal can be adjusted, for example, mechanically and/or electrically. The ability to adjust the adjustable seal allows the sealing effect of the adjustable seal to be adapted, for example, to the operating state of the drive and/or to be readjusted due to aging processes. The provision of a settable adjustable seal allows the sealing effect to be adapted to the sealing effect that is required at any given moment in the mixing apparatus.

In accordance with one embodiment the adjustable seal seals the feed-through in a sealing state as the first sealing operation state; and the adjustable seal is opened in an open state as a second sealing operation state and does not seal the feed-through. In other words, the adjustable seal can be put (for example, reversibly) between the sealing state and the open state. This aspect may be used to put the adjustable seal into the open state only during a first operating state of the drive motor, for example, when the drive drives the drive shaft and, in so doing, the stirring element. If the drive is switched off in a second operating state and/or the drive is not driving the drive shaft at any given time, the adjustable seal can be put into the sealing state. In this case the adjustable seal may be used as a substantially static seal that seals the feed-through only if the drive is at rest. As a result, the adjustable seal is not subject to a load when the stirring element is being driven by the rotational movement of the drive shaft; and, therefore, less strain is put on said adjustable seal. This aspect may reduce the wear of the adjustable seal. In addition, the adjustable seal ensures particularly good sealing protection in resting states of the mixing apparatus, for example, against dust and/or against the ingress of cleaning agents when the mixing apparatus is being cleaned. In addition, the adjustable seal may also seal in the opposite direction against the leakage of the medium out of the mixing container (bag) into the environment (for example, into a clean room). The adjustable seal can be designed as so to be stiffer and/or with a stronger sealing effect as seals that may or may not be additionally present and that have to seal the drive shaft and the feed-through even in the driven and, hence, in the moved operating state.

In accordance with one embodiment the adjustable seal lies close to the drive shaft in the sealing state and is at least partially spaced apart from the drive shaft in the open state. In this case the adjustable seal in the open state can be arranged so as not to be substantially in contact with the drive shaft. As a result, the adjustable seal is not exposed to as great a load by the movement of said drive shaft during operation of the drive shaft, on the one hand; and, on the other hand, the adjustable seal also does not slow down the movement of the drive shaft as much in the operating state of the mixing apparatus.

In a further development of the embodiment the adjustable seal is arranged so as to be completely spaced apart from the drive shaft in the open state. This means that the adjustable seal in the open state does not physically make contact with the drive shaft at any point. This aspect makes it possible to remove the load on the adjustable seal in a particularly good manner during the mixing operation of the mixing apparatus. In order to adequately space the adjustable seal apart from the drive shaft, it may be sufficient to open a small gap between the drive shaft and the adjustable seal. This gap may be, for example, only a single millimeter wide. However, the gap is preferably at least two millimeters wide in order to be able to ensure sufficient spacing even in the event of a slight imbalance of the drive shaft.

In accordance with one embodiment the adjustable seal is designed and provided to assume the sealing state when the drive does not drive the drive shaft and to assume the open state when the drive drives the drive shaft. In this embodiment the adjustable seal is designed, in a manner of speaking, as a stationary seal that seals the feed-through in non-driven resting phases of the mixing apparatus.

In general, the adjustable seal may be designed, for example, as an elastomer that is at least partly pushed away from the drive shaft in the open state and rests against the drive shaft, preferably from all of the radial outer sides, in the sealing state.

In accordance with one embodiment the mixing apparatus comprises a setting apparatus for setting the sealing operation state of the adjustable seal. Actuation of the setting apparatus may cause a change in the sealing operation state of the adjustable seal. The change in the sealing state may be reversible and may occur repeatedly. The setting apparatus may comprise an actuating element for actuating the setting apparatus. The setting apparatus may be designed, in particular, at and/or in the feed-through and/or adjacent to the adjustable seal.

In a further development of this embodiment the setting apparatus is displaceably mounted in the axial direction of the drive shaft. As a result, it is possible to shift the setting direction in the axial direction, for example, closer to the adjustable seal and/or further away from the adjustable seal. As a result, it is possible to actuate the setting of the adjustable seal in a particularly advantageous manner.

In a further development of the embodiment the setting apparatus is designed in a substantially ring shaped manner around the drive shaft. This aspect makes it possible to actuate the adjustable seal, which may also be designed in a substantially ring shaped manner around the drive shaft, over a large area. The setting apparatus and/or the adjustable seal may be designed, in particular, completely around the periphery of the drive shaft.

In accordance with a further development of the embodiment the setting apparatus is designed so as to be substantially conical. A narrow end of the setting apparatus points towards the adjustable seal in a sealing operation state having a high sealing effect. The conical shape means that the setting apparatus has a narrow end and a wide end, which is formed, for example, at least approximately 120%, preferably at least approximately 150%, wider than the narrow end. In this case the conical shape of the adjustable seal may be partially interrupted. The narrow end of the setting apparatus points towards the adjustable seal in the sealing operation state having a high sealing effect. In this sealing operation state having a high sealing effect the setting apparatus may be arranged so as to be spaced apart from the adjustable seal, in order to allow in this way physical contact between the adjustable seal and the drive shaft. If upon actuation the setting apparatus is moved towards the adjustable seal with its narrow end advancing, so that the setting apparatus makes contact with the adjustable seal, then the adjustable seal can be moved in such a way that its position in the feed-through changes, as a result of which the sealing effect of the adjustable seal is also changed. For example, the setting apparatus can be introduced with its narrow end leading between the adjustable seal and the drive shaft. As an alternative or in addition, the setting apparatus can also be introduced between the adjustable seal and an outer housing of the feed-through, in order to change the sealing effect. Preferably, however, the setting apparatus is introduced between the adjustable seal and the drive shaft for purposes of reducing the sealing effect, in order to detach in this manner the adjustable seal from the movable drive shaft. As a result, the wear of the adjustable seal can be reduced in the sealing operation state having a negligible sealing effect.

In one embodiment the mixing apparatus comprises a particle separator in the feed-through. Particle separators are used to separate unwanted particles. A particle separator can provide rotary particle protection, for example, against abrasion, which is generated between the radial shaft sealing ring and the shaft and/or the rolling bearing(s). The particle separator can reduce and/or prevent the ingress of particles into the mixing bag/mixing tank and, in so doing, the contact of the particles with the medium (product). The particle separator is made preferably of (for example, thermoplastic) plastic and may have two retaining lips. The particle separator can fulfill at least one of the following two functions. The particle separator can protect the interior of the mixing container against particles from the feed-through, for example, from a housing at the feed-through. Furthermore, the particle separator can protect the housing against alkalis, acids and/or abrasive materials that are to be mixed in the mixing container. The particle separator can have both of these effects, in particular, in a dual function. Moreover, the particle separator may also be fastened in the feed-through with a particle separator sealing ring, such as, for example, an O-ring. The O-ring may be arranged radially between the particle separator and a housing of the feed-through. The particle separator may be arranged around the drive shaft in the feed-through.

In a further development of this embodiment the particle separator is arranged on a container-side and/or stirring-side feed-through end of the feed-through. In other words, the particle separator may be arranged on the end of the feed-through that faces the interior of the mixing container. Thus, a first side of the particle separator may be in contact with the fluid and/or the solid, which is to be mixed in the mixing apparatus, and faces away from the interior of the mixing container with a second side in the direction of the axis of rotation. In particular, at this exposed position in the feed-through, the particle separator can fulfill the dual function described above.

In accordance with one embodiment the adjustable seal is arranged in a substantially ring shaped manner and/or completely around the drive shaft. In other words, the adjustable seal can be pierced by the drive shaft. In this position the adjustable seal can seal the feed-through and/or the spatial area between the feed-through and the drive shaft in a particularly advantageous way.

In accordance with one embodiment a housing is arranged at the feed-through; and the drive shaft is mounted in the interior of the housing in such a way that it can be moved, in particular, rotated. In this case the housing may comprise at least partly the drive shaft. One or more seals and/or ball bearings can be arranged between the drive shaft and the housing. In particular, the adjustable seal can be arranged in the interior of the housing. The adjustable seal is arranged preferably on an end of the housing that faces away from the mixing container. As a result, the adjustable seal can be protected particularly well against external contamination of the mixing apparatus, such as, for example, dust and/or cleaning agents. The drive, which drives the drive shaft, arranged in the interior of the housing, may be arranged at and/or adjacent to the housing.

In one embodiment the adjustable seal is arranged between the drive shaft and the housing and has a movable sealing region. A movement of the movable sealing region may result in a change in the position and/or location of this movable sealing region in the interior of the housing. The movement can cause a change in the sealing effect of the adjustable seal and, as a result, an adjustment of the sealing operation state of the adjustable seal. The movable sealing region can be arranged, for example, so as to be adjacent to and/or adjoining the drive shaft. The movable sealing region may be elastically deformable. The movement of the movable sealing region may comprise an elastic deformation, in particular, an at least partial compression and/or at least partial stretching of the movable sealing region. In addition, the adjustable seal may have a static sealing region, the position and/or location of which is substantially invariable. The static sealing region may be designed, for example, adjacent to the housing.

In a further development of this embodiment the housing has a reinforcement on a drive-side end of the feed-through. At least at this point the housing is mechanically reinforced, for example, with a metal ring, which is arranged, for example, around the drive-side housing from the outside. The reinforcement may be at least partially metallic. As a result, the mechanical rigidity of the housing surface can be increased in this particularly stressed area, since, for example, a housing made of plastic does not always exhibit by itself sufficiently high mechanical rigidity. Since the, for example, movable adjustable seal can be arranged in this drive-side area, it can be expected that the highest mechanical load will be acting at and on this portion of the housing.

In one embodiment the mixing apparatus comprises at least one additional permanent seal that seals the feed-through independently of the sealing operation state of the adjustable seal. This at least one permanent seal ensures that the feed-through will be sealed even in, for example, the opened state of the adjustable seal and possibly also in sealing operation states having a weaker and/or negligible sealing effect. The permanent seal may be designed and provided to make contact with the drive shaft, even in a driven state, i.e., in a moved state, and, in so doing, to seal the feed-through.

In accordance with one embodiment the mixing apparatus comprises the drive, arranged outside of the mixing container, for driving the drive shaft and/or the mixing container, in the interior of which the fluid and/or the solid can be arranged.

In accordance with one embodiment the mixing apparatus comprises the mixing container, in the interior of which the fluid and/or solid can be arranged. In this case the mixing container has an at least partially flexible container wall; and/or the mixing container is designed as a bioreactor bag and/or mixing bag and/or pallet tank. The mixing bag may be designed, in particular, as a disposable bag, such as, for example, a "single-use bag". In this case the mixing container may have a flexible container wall, which may be formed, for example, of a flexible plastic material, substantially from all sides. The mixing container may have a stiffening around the feed-through and/or a coupling apparatus for coupling to the mixing container receptacle.

One aspect relates to a method for operating a mixing apparatus for mixing a fluid or solid, said method comprising the steps:
receiving the fluid and/or solid in a mixing container;
mixing the fluid and/or solid, arranged in the mixing container, with a stirring element, arranged at least partly in the interior of the mixing container;
driving the stirring element with a drive shaft that is driven by a drive, arranged outside of the mixing container, and that is fed through a container wall of the mixing container at a feed-through; and
putting a settable adjustable seal for sealing the feed-through into one of at least two sealing operation states having different sealing effects.

The method may be carried out, in particular, in and/or by a mixing apparatus in accordance with the aspect described above. Therefore, all of the statements made in conjunction with the mixing apparatus also apply to the method and vice versa.

In one embodiment of the method the adjustable seal is put into a sealing state as a first sealing operation state, in which the adjustable seal seals the feed-through, in particular, when the drive shaft is not driven. Furthermore, the adjustable seal is put into an open state as a second sealing operation state, in which it does not seal the feed-through and/or seals the feed-through in a reduced manner, in particular, when the drive shaft is driven. In this embodiment the adjustable seal is used, for example, as a static seal that seals the feed-through only in a resting state of the mixing apparatus and is put into the open state during operation of the mixing apparatus.

In the context of this invention the terms "substantially" and/or "approximately" may be used to include a deviation of up to 5% from a numerical value following the term, a deviation of up to 5° from a direction following the term and/or an angle following the term.

Terms, such as top, bottom, above, below, etc., refer to the reference system of the earth in an operating position of the subject matter of the invention, unless stated otherwise.

The invention is described below in more detail with reference to exemplary embodiments shown in the figures. In this case the same or similar reference numerals may designate the same or similar features of the embodiments. Individual features, shown in the figures, may be implemented in other exemplary embodiments.

BRIEF DESCRIPTION OF THE DRAWINGS

FIG. 5A shows a cross section of a feed-through with an adjustable seal in a sealing state;

FIG. 5B shows a cross section of the feed-through, shown in FIG. 5A, with the adjustable seal in a sealing state; and FIG. 5C shows a cross section of the feed-through, shown in FIG. 5A, with the adjustable seal in an open state.

DETAILED DESCRIPTION

Figure 1:
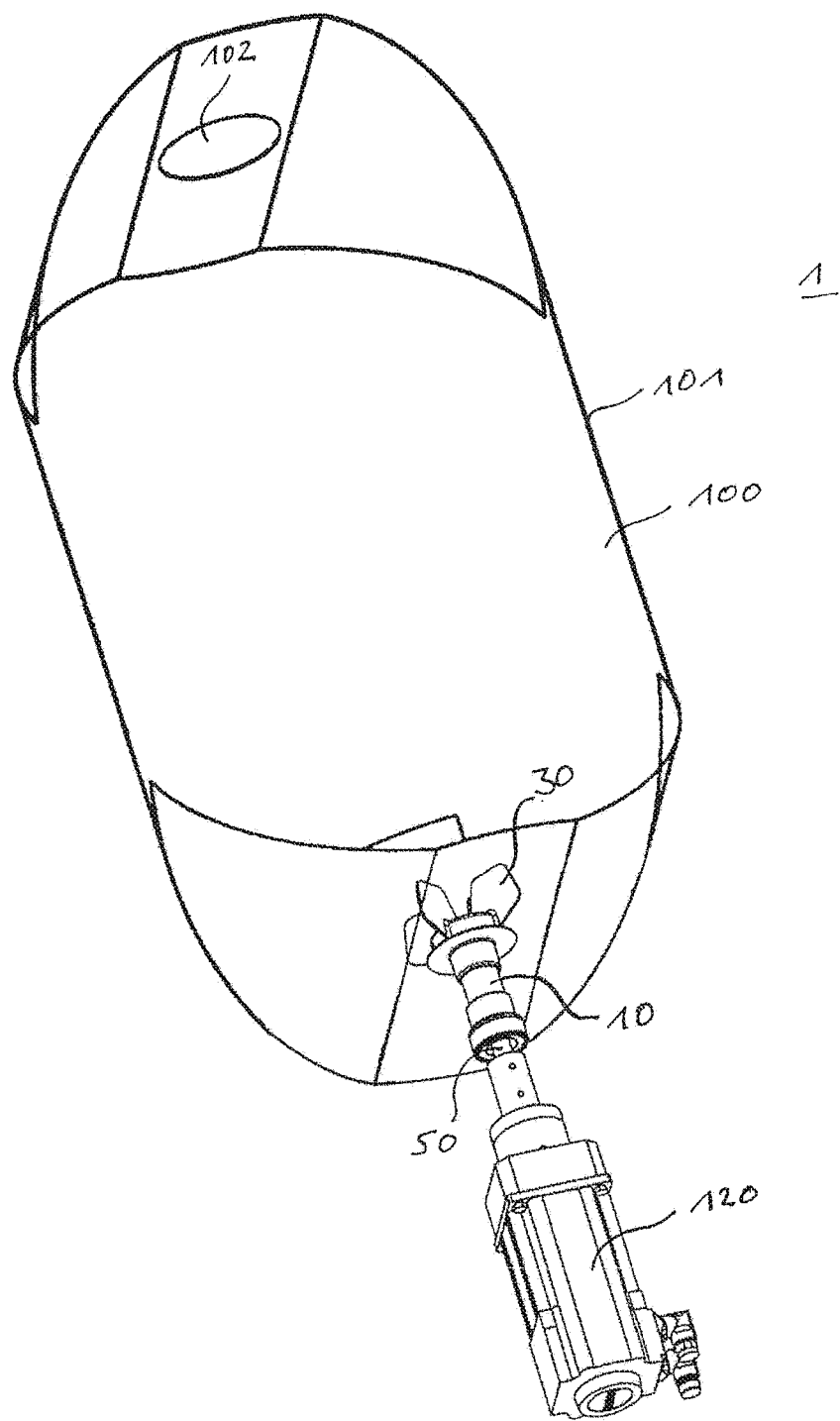
FIG. 1 shows in a diagrammatic representation a perspective view of a mixing apparatus that is intended for mixing a fluid and/or solid and that comprises a mixing container.

FIG. 1 shows in a diagrammatic representation a perspective view of a mixing apparatus 1 for mixing a fluid and/or solid, which may be arranged in a mixing container 100.

The mixing apparatus 1 comprises a drive 120, which may be designed, for example, as a motor, in particular, as an electric motor. The drive 120 drives a drive shaft 50, which is fed through a feed-through (or a feed-through passage) 10 into the interior of the mixing container 100. The drive 120 is used to drive a stirring element 30, which is arranged in the interior of the mixing container 100 and is designed and provided for mixing a medium in the interior of the mixing container 100.

The drive 120, the mixing container 100 and/or the stirring element 30 may be designed as part of the mixing apparatus 1. As an alternative, one, two or all three of these components may be designed as a respective separate component, which is not designed as part of the mixing apparatus 1, but rather only for coupling to the mixing apparatus 1.

The mixing container 100 may be designed as a mixing bag and/or as a bioreactor bag. The mixing container 100 has a container wall 101, which may be at least partly formed of a flexible material, such as a flexible plastic material. The mixing container 100 may include an inlet port 102, through which the fluid and/or the solid may be filled into and/or drained out of the interior of the mixing container 100. In the exemplary embodiment shown, the inlet port 102 is arranged on one end of the mixing container 100, where said end is designed so as to be opposite the feed-through 10 in the container wall 101.

In one exemplary embodiment the feed-through 10 may be arranged at a lower end of the mixing container 100. The inlet port 102 may be arranged, for example, on an upper end of the mixing container 100.

In one exemplary embodiment the mixing container 100 may also be designed as a pallet tank for receiving a solid.

Figure 2:
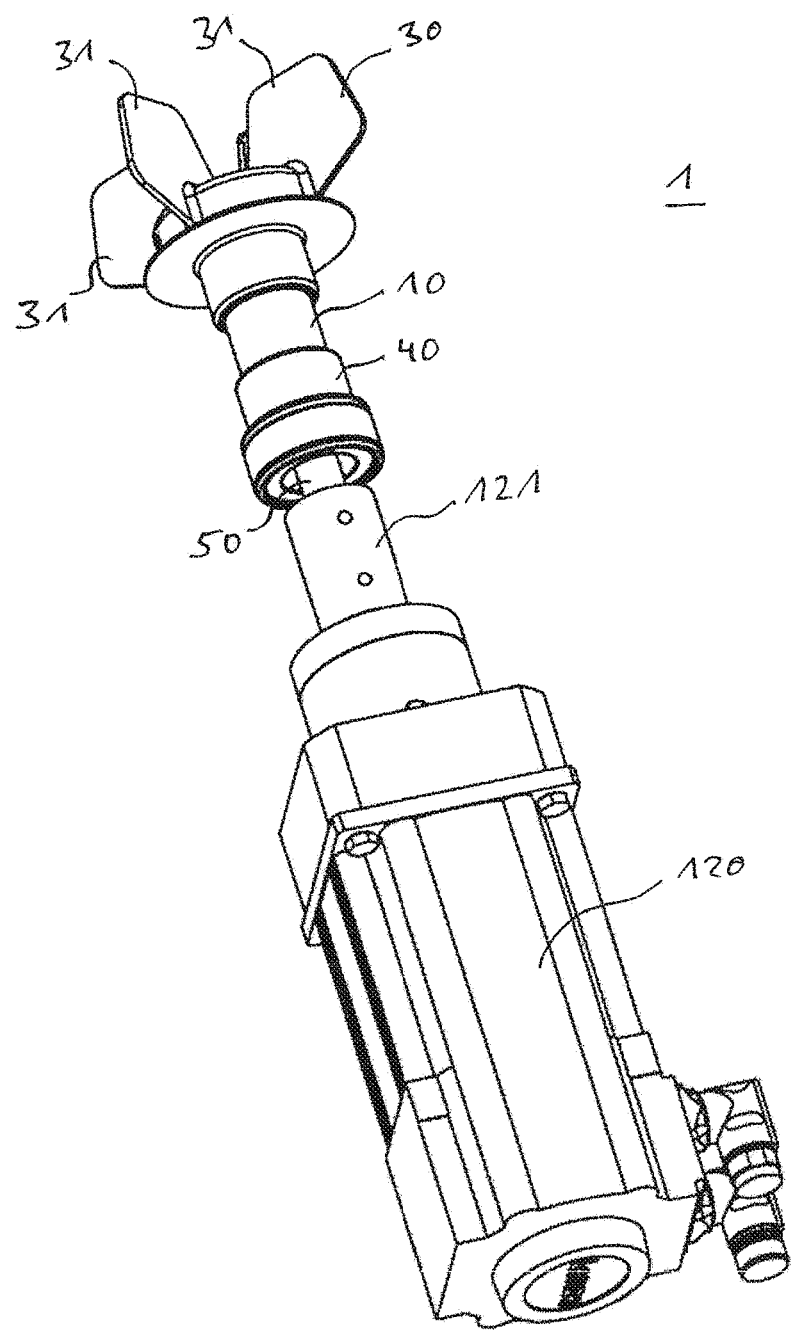
FIG. 2 shows a perspective view of a feed-through, a stirring element and a drive of a mixing apparatus.

FIG. 2 shows a perspective view of the feed-through 10, the stirring element 30 and the drive 120 of the mixing apparatus 1. The drive 120 is used to drive a drive shaft 50, of which only a small portion is shown in FIG. 2. The drive 120 may be connected to the drive shaft 50 through a clutch 121. The clutch 121 may be designed, in particular, as a feather key coupling. The drive 120 can drive the drive shaft 50, for example, to a rotational movement about its longitudinal axis.

The drive shaft 50 is arranged in the interior of the feed-through 10, which is designed at an opening in the container wall 101 of the mixing container 100. In this embodiment the feed-through 10 is designed as a shaft feed-through, inside of which the drive shaft 50 is fed through the container wall 101. In this case the drive shaft 50 is arranged in such a way that it pierces and/or passes through the container wall 101 of the mixing container 100. The feed-through 10 comprises a housing 40, which may be formed, for example, of a thermoplastic material. The drive shaft 50 is mounted in the housing 40. The housing 40 can be designed and provided for both supporting the drive shaft 50 and/or for improved sealing.

The stirring element 30 may have a plurality of stirring blades 31, which protrude into the interior of the mixing container 100. In the exemplary embodiment shown, the stirring element 30 has four stirring blades 31. In other embodiments the stirring element 30 may include more or fewer stirring blades 31. As an alternative, the stirring element 30 may also have a different shape, for example, may be formed in a spiral and/or bowl shaped manner.

The feed-through 10 is designed as a connection between the drive 120 and the stirring element 30. In the embodiment shown, the feed-through 10 is arranged locally between the stirring element 30 and the drive 120.

Figure 3:
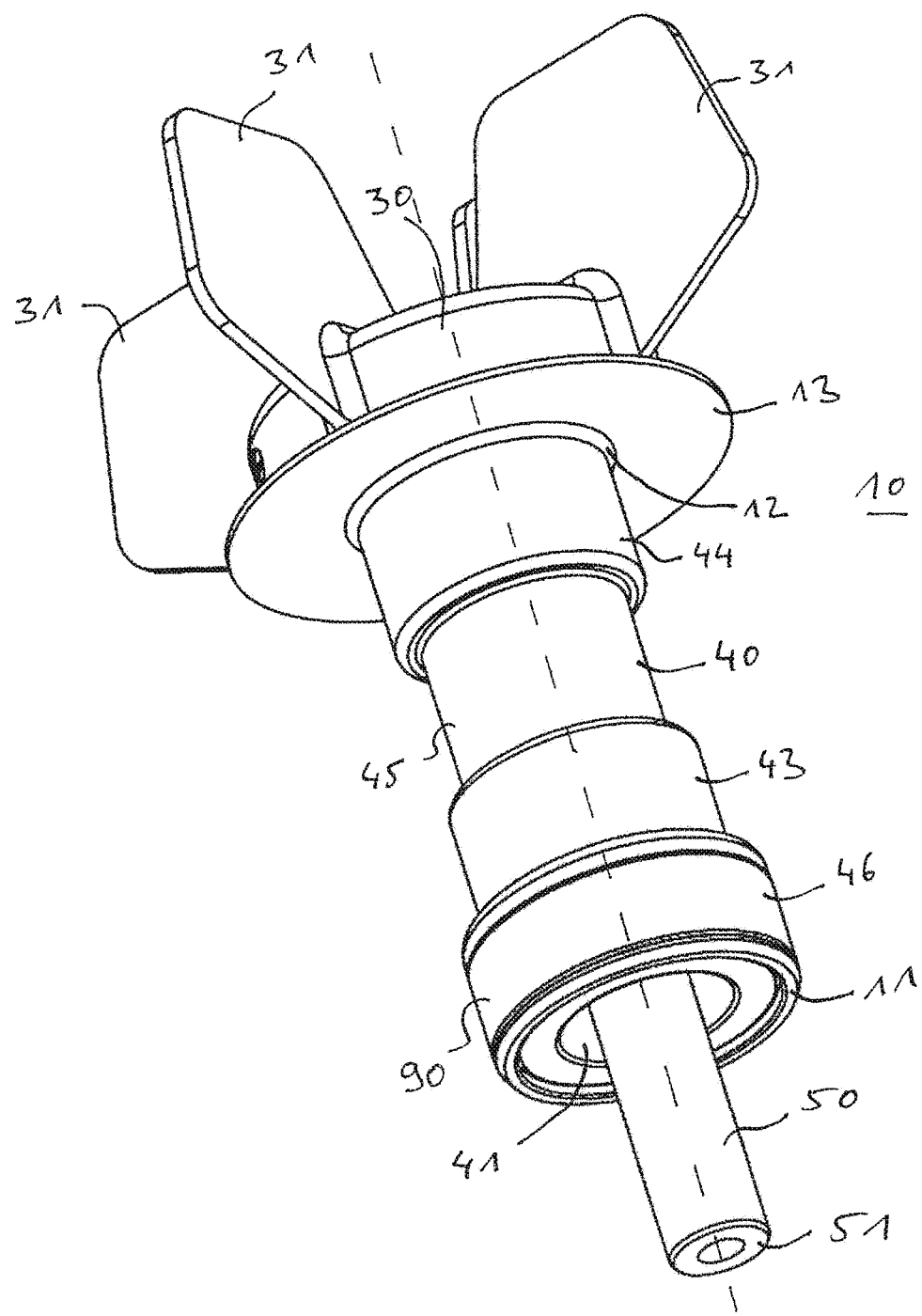
FIG. 3 shows a perspective view of a feed-through and a stirring element of a mixing apparatus.

FIG. 3 shows the feed-through 10 of the mixing apparatus 1 together with the stirring element 30, fastened thereto, in a perspective view. The housing 40 of the feed-through 10 is designed to be substantially rotationally symmetrical with respect to an axis of rotation R of the drive shaft 50. The axis of rotation R of the drive shaft 50 extends along a longitudinal axis and/or cylinder axis of the drive shaft 50. The axis of rotation R of the drive shaft 50 may also be designed as the axis of rotation of the stirring element 30 at the same time.

On the drive-side feed-through end 11 of the feed-through 10 a drive-side shaft end 51 protrudes from a drive-side housing opening 41 out of the housing 40. The drive-side shaft end 51 is designed and provided to be contacted by the drive 120 and/or the clutch 121. In particular, the drive 120 can be coupled to the drive-side shaft end 51 through the clutch 121.

The housing 40 is designed so as to be substantially rotationally symmetrical in the shape of a cylinder, the cylinder axis of which coincides with the axis of rotation R. The housing 40 may be designed so as to be substantially circular in the cross section along a plane, arranged perpendicular to the axis of rotation R, in particular, substantially along its entire cylinder height. The housing 40 may change its (cylinder) diameter once or several times along the axis of rotation R.

The housing 40 has a central housing region 45, which has the smallest housing diameter in the exemplary embodiment shown. In this case the term housing diameter is defined as the expansion of the housing 40 perpendicular to the axis of rotation R, i.e., in the radial direction. Adjacent to the drive side and the stirring side at the central region 45, the housing 40 has in each case a region, which is widened in relation to the central region 45, i.e., a housing region having a housing diameter that is widened in relation to the central region 45.

On the drive side the housing 40 (for example, adjacent to the central housing region 45) has a first housing shoulder 43, which has a wider housing diameter than the central housing region 45. On the stirring side the housing 40 has a second housing shoulder 44, which may be, for example, adjacent to the central region 45 on the stirring side and which may have a wider housing diameter compared to said central region. At the transition of the central housing region 45 to both the first housing shoulder 43 and the second housing shoulder 44, the housing 40 has in each case a housing stage.

A flange 13 is formed on a stirring-side and/or container-side feed-through end 12 of the feed-through 10. The flange 13 reinforces the container wall 101 of the mixing container 100 and may be designed as a mixing container receptacle and/or reinforcement. The flange 13 may be designed as part of the mixing container 100 and/or as part of the feed-through 10. In the exemplary embodiment shown, the second housing shoulder 44 extends with a substantially constant housing diameter from the central housing region 45 as far as up to the stirring-side feed-through end 12, on which the flange 13 is formed.

The first housing shoulder 43 extends with a substantially constant housing diameter from the drive-side end of the central region 45 as far as up to a third housing shoulder 46 of the housing 40.

The third housing shoulder 46 has a housing diameter, which is widened in relation to the first housing shoulder 43. The third housing shoulder 46 extends with a substantially constant housing diameter from the drive-side end of the first housing shoulder 43 as far as up to the drive-side end of the feed-through 10. The drive-side housing opening 41, which is formed in a substantially ring shaped manner around the drive shaft 50, is designed and arranged on this drive-side feed-through end 11.

The housing 40 comprises a cavity from the drive-side feed-through end 11 as far as up to the stirring-side feed-through end 12, in which the drive shaft 50 is arranged and/or in which it is laid. In this case the drive shaft 50 may protrude from the cavity, enclosed by the housing 40, and, in particular, on both the drive side and the stirring side.

A reinforcement 90, in particular, a reinforcing ring, which may be designed, for example, as a metallic reinforcing ring, may be designed at least partly around the third housing shoulder 46. Reinforcement 90 is designed and provided to mechanically reinforce and/or stabilize the third housing shoulder 46. For this purpose, the reinforcement 90 may be designed in the shape of a ring around the axis of rotation R of the drive shaft 50 and may be formed radially outwards around the third housing shoulder 46 of the housing 40.

Figure 4:
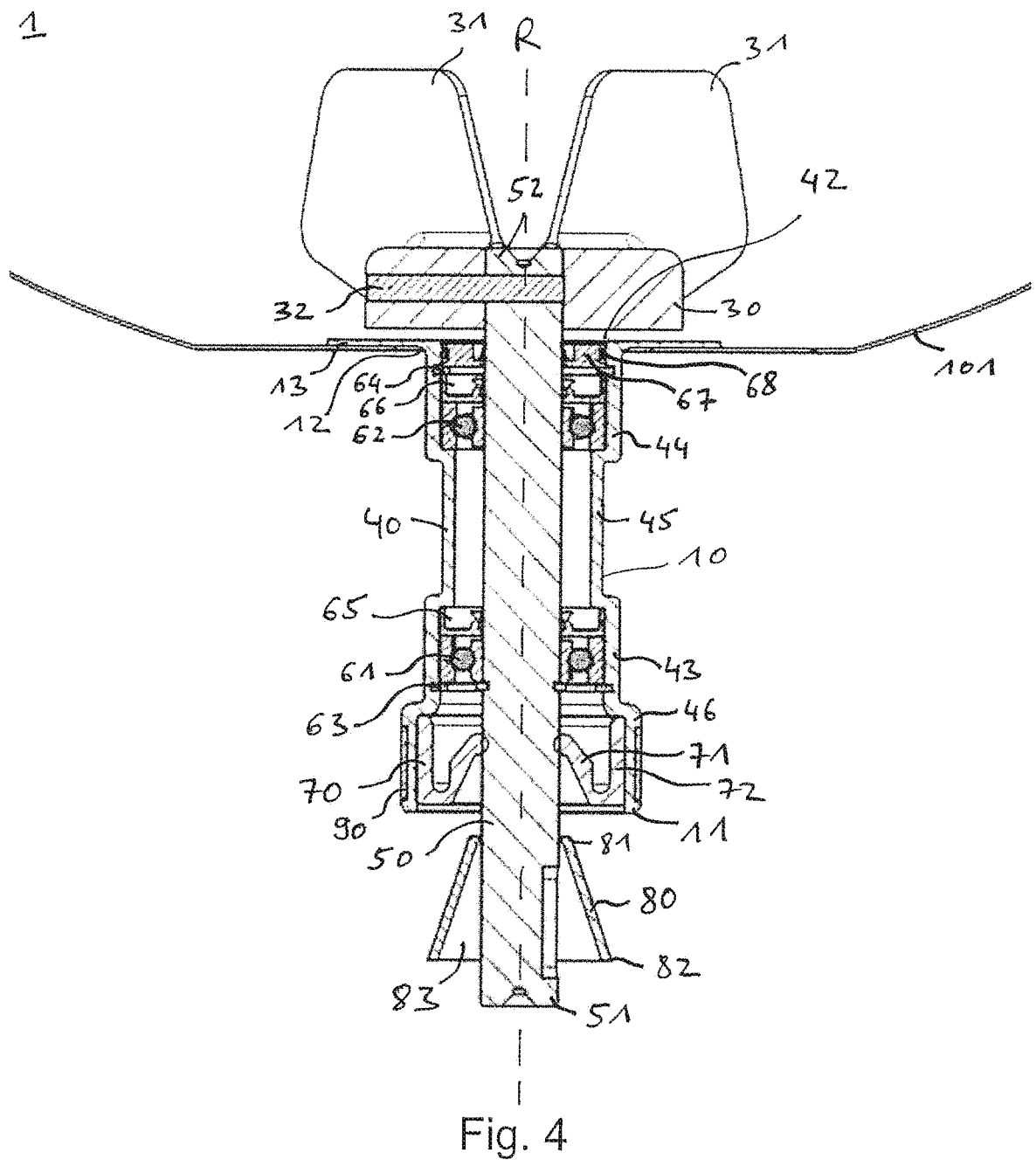
FIG. 4 shows a cross section of a feed-through, fed through a container wall, with a stirring element of a mixing apparatus.

FIG. 4 shows a cross section of a mixing apparatus 1 at the feed-through 10.

The drive shaft 50 is formed so as to be substantially rod-shaped and extends from the drive-side shaft end 51 to its stirring-side shaft end 52 along the axis of rotation R. In this case the drive shaft 50 passes completely through the housing 40 of the feed-through 10 from the drive-side feed-through end 11 as far as up to the stirring-side feed-through end 12. In particular, the drive shaft 50 passes though the container wall 101 of the mixing container 100, shown only partially in FIG. 4.

On the stirring-side shaft end 52 of the drive shaft 50, the drive shaft 50 is coupled to the stirring element 30. For this purpose, a connector 32 is provided that may be designed, for example, as a screw. The connector 32 may be designed and arranged partially in the interior of the drive shaft 50 and partially in the interior of the stirring element 30 and may provide a positive and/or non-positive connection between the stirring element 30 and the drive shaft 50. The drive shaft 50 is mounted in the interior of the housing 40 through at least one bearing. In the exemplary embodiment shown, the drive shaft 50 is mounted in the interior of the housing 40 with a first bearing 61 and a second bearing 62 in a manner allowing rotation about the axis of rotation R. The two bearings 61 and 62 are spaced apart from one another in the direction of propagation of the axis of rotation R. In this case the first bearing 61 is designed in the interior of the first housing shoulder 43, and the second bearing 62 is designed in the interior of the second housing shoulder 44. The first bearing 61 and the second bearing 62 may be designed in each case as a deep groove ball bearing.

The first bearing 61 is clamped between a housing stage at the transition from the central housing region 45 to the first housing shoulder 43, on the one hand, and a snap ring 63, on the other hand, in such a way that it is substantially non-displaceable and/or immovable along the axis of rotation R. The second bearing 62 is clamped between the housing stage at the transition from the central housing region 45 to the second housing shoulder 44, on the one hand, and a second snap ring 64, on the other hand, in such a way that it is substantially non-displaceable and/or immovable along the axis of rotation R.

A respective seal is designed on the side of the respective bearing 61 and 62, which faces the stirring element 30. In this way a first seal 65 is arranged between the first bearing 61 and the housing stage of the housing 40. Between the second bearing 62 and the second snap ring 64 there is arranged a second seal 66. The first seal 65 and/or the second seal 66 may each be designed as a permanent seal, in particular, as a radial shaft sealing ring. The first and/or second seal(s) 65 and/or 66 is/are designed in each case as a dynamic seal. This means that the respective seal 65 or 66 rests in a sealing manner against both movable and immovable parts of the mixing apparatus 1. In this embodiment both the first seal 65 and the second seal 66 are arranged between the movable drive shaft 50 and the housing 40, thus, sealing these two components of the mixing apparatus 1 off from each other. The first seal 65 and the second seal 66 dynamically seal the feed-through 10 between the drive shaft 50 and the housing 40, for example, against leakage of the medium out of the mixing container 100 during the mixing process.

The housing 40 may be formed of a thermoplastic material that may be welded by way of the flange 13 to the mixing container 100, which may also be formed of plastic.

On the stirring-side feed-through end 12, a stirring-side housing opening 42 is formed, from which the drive shaft 50 protrudes out of the housing 40 along the axis of rotation R. On the stirring-side feed-through end 12, in particular, in and/or at the stirring-side housing opening 42, a particle separator 67 is designed that can be sealed by a particle separator seal 68. The particle separator seal 68 may be designed, for example, as an O-ring and is arranged in the radial direction between the particle separator 67 and the housing 40, in particular, a stirring-side end of the second housing shoulder 44. The particle separator 67 may be designed and provided to leave some or all of the particles, generated inside the housing 40 during operation, inside the housing 40, and, in so doing, outside of the mixing container 100. The particle separator 67 may also be designed and provided to form a barrier and a protection for the second seal 66, in particular, against alkalis, acids and/or abrasive materials from the interior of the mixing container 100.

The first housing shoulder 43, the first bearing 61, the first snap ring 63 and the first seal 65 may each be designed as a drive-side component of the feed-through 10, i.e., as a drive-side housing shoulder 43, as a drive-side bearing 61, as a drive-side snap ring 63 and/or as a drive-side seal 65.

The second bearing 62, the second housing shoulder 44, the second snap ring 64 and/or the second seal 66 may each be designed as a respective stirring-side component of the feed-through 10, i.e., as a stirring-side housing shoulder 44, as a stirring-side bearing 62, as a stirring-side snap ring 64 and/or as a stirring-side seal 66.

The drive shaft 50, which may be formed of a plastic material, is fed through the housing 40. The stirring element 30, which may also be formed of plastic, is designed on the stirring shaft end 52. The connector 32 is used for mechanically connecting the drive shaft 50 to the stirring element 30. On the opposite end of the drive shaft 50, i.e., the drive-side shaft end 51, the drive shaft 50 is positively connected to the drive 120 through the clutch 121.

The housing 40, a major portion of the drive shaft 50, the clutch 121 and the drive 120 are arranged outside of the mixing container 100. In this case the housing 40 is adjacent to at least the mixing container 100 or the mixing container receptacle. As a result, the housing 40 of the feed-through 10 can protrude at least partly into the interior of the mixing container 100. The flange 13 may be arranged, for example, inside the mixing container 100.

The third housing shoulder 46 of the housing 40 is designed adjacent to the drive-side feed-through end 11. In the exemplary embodiment shown, the third housing shoulder 46 has a substantially constant housing diameter, which is designed so as to be larger than the housing diameter of the first housing shoulder 43 and/or the second housing shoulder 44 and, thus, also larger than the housing diameter of the central housing region 45.

In the interior of the third housing shoulder 46 an adjustable seal 70 is provided between a housing wall of the housing 40 and the drive shaft 50. The adjustable seal 70 may be configured as a static seal, in particular, as a static elastomeric seal. The adjustable seal 70 is designed and provided to seal the mixing container 100 during standstill of the mixing apparatus 1. During operation of the mixing apparatus 1, i.e., when the stirring element 30 is being driven, the adjustable seal 70 can be detached from the drive shaft 50 with a setting apparatus 80. In the standstill mode of the mixing apparatus 1, the adjustable seal 70 can be reversibly coupled to the drive shaft 50 again.

The adjustable seal 70 may be designed in a substantially ring shaped manner around the axis of rotation R and around the drive shaft 50. For this purpose the adjustable seal 70 may have a static sealing region 72, which adapts from radially inwards to the housing 40, more precisely to the third housing shoulder 46 and/or is adjacent thereto. This static sealing region 72 of the adjustable seal 70 is designed so as to be substantially immovable and does not substantially change its shape and/or position and/or its degree of compression in the interior of the housing 40. The static sealing region 72 may be formed in a substantially tube shaped and/or hose shaped manner around the axis of rotation R and spaced apart therefrom.

A movable sealing region 71 of the adjustable seal 70 is formed substantially adjacent to the static sealing region 72, where said adjustable seal connects the static sealing region 72 to the drive shaft 50 in the sealing operation state shown in FIG. 4. For this purpose the movable sealing region 71 in the sectional view shown may be designed so as to be substantially transverse to the axis of rotation R, i.e., at an angle to the axis of rotation R, along a plane, in which the axis of rotation R is arranged. In the exemplary embodiment shown, the movable sealing region 71 extends away from the drive shaft 50 at angle to the axis of rotation R as far as up to the housing end of the housing 40 on the drive-side feed-through end 11. There, a sealing transition region is formed between the movable sealing region 71 and the static sealing region 72, which connects these two sealing regions 71 and 72 to one another.

The reinforcement 90 is designed around the third housing shoulder 46. The reinforcement 90 may be designed, for example, as a metal ring and shrunk onto this part of the housing 40, as a result of which this part of the housing is stabilized.

The setting apparatus 80 may be designed as a decoupling mechanism. The setting apparatus 80 is designed in a substantially conical manner around the drive shaft 50.

In this case the setting apparatus 80 has a narrow end 81, which faces the drive-side feed-through end 11 in the position shown. In addition, the setting apparatus 80 also has a wide end 82, which faces away from the feed-through 10 in the embodiment shown. The narrow end 81 is designed as a stirring-side end of the setting apparatus 80, while the wide end 82 is designed as a drive-side end of the setting apparatus 80. The outer diameter of the setting apparatus 80 increases from the stirring-side end 81 to the drive-side end 82; in the exemplary embodiment shown, it increases substantially steadily.

In the interior the setting apparatus 80 has a passage 83, which is designed as a cavity and through which the drive shaft 50 passes. The setting apparatus 80 is designed so as to be substantially rotationally symmetrical with respect to the axis of rotation R and is arranged around the drive shaft 50 like a sleeve and/or a cuff.

FIGS. 5A, 5B and 5C show a cross section of the housing 40 of the feed-through 10, wherein the adjustable seal 70 is put into different sealing operation states.

FIGS. 5A and 5B show in essence the state of the adjustable seal 70 that has already been described in conjunction with FIG. 4. In this case the setting apparatus 80 is not shown in FIG. 5A. FIG. 5B shows how the setting apparatus 80 is moved in the direction of the arrow, i.e., parallel to the axis of rotation R, towards the drive-side feed-through end 11 and, in particular, towards the adjustable seal 70.

In the embodiment shown in FIGS. 5A and 5B, the movable sealing region 71 lies close to the drive shaft 50. In so doing, the interior of the housing 40 and, thus, the interior of the feed-through 10 are sealed from the outside atmosphere and vice versa. In the situation shown in FIG. 5B, the adjustable seal 70 is put into a sealing state as a sealing operation state by exerting and/or having a, for example, maximum sealing effect. In this case the setting apparatus 80 is arranged so as not to be in contact with the adjustable seal 70, for example, is arranged completely outside the housing 40. In particular, the setting apparatus 80 and the narrow end 81 of the setting apparatus 80 are arranged at a distance from the adjustable seal 70, in particular, spaced apart in the direction of propagation of the axis of rotation R.

In FIG. 5C, the setting apparatus 80 is pushed into the interior of the housing 40. In this case the stirring-side end 81 of the setting apparatus 80 penetrates into the drive-side feed-through end 11. The stirring-side end 81 of the setting apparatus 80 is arranged between the movable sealing region 71 of the adjustable seal 70 and the drive shaft 50. As a result, a gap opens between the adjustable seal 70 and the drive shaft 50. In other words, the setting apparatus 80 keeps the adjustable seal 70 spaced apart from the drive shaft 50. In this sealing operation state the adjustable seal 70 no longer seals the housing 40 optimally; and the adjustable seal 70 is in an open state having a weaker and reduced sealing effect.

In the open state of the adjustable seal 70, the static sealing region 72 of the adjustable seal 70 has substantially the same shape, position and compression as in the sealing state. Only the movable sealing region 71 of the adjustable seal 70 is elastically deformed by the mechanical action of the setting apparatus 80. In this case the deformation of the adjustable seal 70 takes place elastically and/or reversibly. In other words, moving the setting apparatus 80 along the axis of rotation R out of the third housing region 46 restores once again the sealing operation state, shown in FIGS. 5A and 5B, in which the adjustable seal 70 seals the interior of the housing 40.

The movement of the setting apparatus 80 may take place and/or be triggered mechanically and/or electrically.

The adjustable seal 70 may be designed as a seal having a particularly strong sealing effect, in particular, as a seal with a higher sealing effect than the first and/or second seal(s) 65 and/or 66. As a result, a particularly strong and/or high sealing effect can be achieved, in particular, in resting states of the mixing apparatus 1.

Such a strong sealing effect can be provided and/or caused, for example, by an adjustable seal 70, in particular, by the movable sealing region 71 that lies flush and/or close to the drive shaft 50. This feature would slow down the drive shaft 50 during the mixing operation and/or lead to severe abrasion. Therefore, during operation of the mixing apparatus 1 the adjustable seal 70 is detached from the drive shaft 50, in particular, is arranged so as to be spaced apart from it, with the setting apparatus 80. In operation, the first seal 65 and the second seal 66 continue to seal the interior of the housing against the fluid and/or the solid in the interior of the mixing container 100. In the open state the adjustable seal 70 may be designed so as not to be in contact with the drive shaft 50.

LIST OF REFERENCE NUMERALS AND SYMBOLS 1 mixing apparatus
10 feed-through 11 drive-side feed-through end
12 container-side/stirring-side feed-through end
13 flange
30 stirring element
31 stirring blade
32 connector
40 housing
41 drive-side housing opening
42 stirring-side housing opening
43 first housing shoulder
44 second housing shoulder
45 central housing region
46 third housing shoulder
50 drive shaft
51 drive-side shaft end
52 stirring-side shaft end
61 first bearing
62 second bearing
63 first snap ring
64 second snap ring
65 first seal
66 second seal
67 particle separator
68 particle separator seal
70 adjustable seal
71 movable sealing region
72 static sealing region
80 setting apparatus
81 narrow end
82 wide end
83 passage
90 reinforcement
100 mixing container
101 container wall
102 inlet port
120 drive
121 clutch
R axis of rotation

What is claimed is:

1. A mixing apparatus for mixing a fluid and/or a solid, comprising:
    a mixing container comprising a container wall defining an interior and configured to contain the fluid and/or the solid;
    a feed-through passage extending through the container wall;
    a stirring element arranged at least partly in the interior of the mixing container;
    a drive shaft extending through the feed-through passage and configured to drive the stirring element to mix the fluid and/or the solid contained in the mixing container, wherein the drive shaft comprises a drive-side shaft end configured to couple a drive arranged outside of the mixing container to the drive shaft;
    a radial shaft seal arranged in the feed-through passage and resting in a sealing manner against the drive shaft;
    an adjustable seal that produces a first sealing effect with respect to the feed-through passage in a first sealing operation state and produces a second sealing effect with respect to the feed-through passage that differs from the first sealing effect in a second sealing operation state; and
    a particle separator arranged in the feed-through passage, wherein the feed-through passage comprises a container-side feed-through end, and
    wherein the particle separator is arranged at the container-side feed-through end and provides a barrier against entry of abrasive particles into the interior of the mixing container resulting from rotational movement generated between the radial shaft seal and the drive shaft and contact of the abrasive particles with the fluid and/or the solid contained in the mixing container.

2. The mixing apparatus as claimed in claim 1, wherein:
    the adjustable seal seals the feed-through passage in a sealing state as the first sealing operation state, and
    the adjustable seal is opened in an open state that does not seal the feed-through passage as the second sealing operation state.

3. The mixing apparatus as claimed in claim 2, wherein the adjustable seal lies against the drive shaft in the sealing state and is at least partially spaced apart from the drive shaft in the open state.

4. The mixing apparatus as claimed in claim 2, wherein the adjustable seal is completely spaced apart from the drive shaft in the open state.

5. The mixing apparatus as claimed in claim 2, wherein the adjustable seal is configured to assume:
    the sealing state when the drive is not positioned to drive the drive shaft, and
    the open state when the drive is positioned to drive the drive shaft.

6. The mixing apparatus as claimed in claim 1, further comprising a setting apparatus for switching the adjustable seal between the first sealing operation state and the second sealing operation state.

7. The mixing apparatus as claimed in claim 6, wherein the setting apparatus is mounted to displace in axial directions of the drive shaft.

8. The mixing apparatus as claimed in claim 6, wherein the setting apparatus is substantially ring shaped around the drive shaft.

9. The mixing apparatus as claimed in claim 1, further comprising a setting apparatus for switching the adjustable seal between producing the first sealing effect and producing the second sealing effect, wherein the setting apparatus is substantially conical and tapers towards a narrow end that is pointed towards the adjustable seal.

10. The mixing apparatus as claimed in claim 9, wherein the narrow end of the adjustable seal rests sealingly against the drive shaft in the first sealing operation state, and rests non-sealingly against the setting apparatus in the second sealing operation state.

11. The mixing apparatus as claimed in claim 1, wherein the adjustable seal is substantially ring shaped around the drive shaft.

12. The mixing apparatus as claimed in claim 1, further comprising:
    a housing arranged at the feed-through passage and defining an interior, wherein the drive shaft is movably mounted in the interior of the housing.

13. The mixing apparatus as claimed in claim 12, wherein the adjustable seal is arranged between the drive shaft and the housing and comprises a movable sealing region.

14. The mixing apparatus as claimed in claim 12, wherein the housing comprises a reinforcement on a drive-side end of the feed-through passage.

15. The mixing apparatus as claimed in claim 1, further comprising at least one additional, permanent seal, which seals the feed-through passage independently of the sealing operation states of the adjustable seal.

16. The mixing apparatus as claimed in claim 1, wherein the drive is arranged outside of the mixing container for driving the drive shaft and/or the mixing container in which the fluid and/or the solid is contained.

17. The mixing apparatus as claimed in claim 1, wherein the mixing container containing the fluid and/or the solid
- comprises an at least partially flexible container wall; and/or
- is configured as a bioreactor bag and/or as a mixing bag.

18. A mixing apparatus for mixing a fluid and/or a solid, comprising:
- a mixing container comprising a container wall defining an interior and configured to contain the fluid and/or the solid;
- a feed-through passage_extending through the container wall;
- a stirring element arranged at least partly in the interior of the mixing container;
- a drive shaft extending through the feed-through passage and configured to drive the stirring element to mix the fluid and/or the solid contained in the mixing container, wherein the drive shaft comprises a drive-side shaft end configured to couple a drive arranged outside of the mixing container to the drive shaft;
- a radial shaft seal arranged in the feed-through passage and resting in a sealing manner against the drive shaft;
- a housing arranged at the feed-through passage and defining an interior, wherein the drive shaft is movably mounted in the interior of the housing;
- an adjustable seal that produces a first sealing effect with respect to the feed-through passage in a first sealing operation state and produces a second sealing effect with respect to the feed-through passage that differs from the first sealing effect in a second sealing operation state, wherein the adjustable seal annularly surrounds the drive shaft, and the housing annularly surrounds the adjustable seal;
- a setting apparatus that annularly surrounds the drive shaft for switching the adjustable seal between the first sealing operation state and the second sealing operation state; and
- a particle separator arranged in the feed-through passage,
- wherein the adjustable seal is arranged between the drive shaft and the housing,
- wherein the adjustable seal contacts the housing and extends radially from the housing to the drive shaft in the first sealing operation state,
- wherein the adjustable seal contacts the housing and extends radially from the housing to the setting apparatus in the second sealing operation state,
- wherein the adjustable seal contacts the housing and extends radially from the wherein the feed-through passage comprises a container-side feed-through end, and
- wherein the particle separator is arranged at the container-side feed-through end and provides a barrier against entry of abrasive particles into the interior of the mixing container resulting from rotational movement generated between the radial shaft seal and the drive shaft and contact of the abrasive particles with the fluid and/or the solid contained in the mixing container.

19. The mixing apparatus as claimed in claim 18, wherein the adjustable seal comprises:
- a static sealing region at least in a circumferential area in which the adjustable seal contacts the housing, and
- a movable sealing region at least in a circumferential area in which the adjustable seal contacts the drive shaft and/or the setting apparatus.

* * * * *